United States Patent [19]

Okada et al.

[11] Patent Number: 5,780,633

[45] Date of Patent: Jul. 14, 1998

[54] PROCESS FOR THE PREPARATION OF INDOLIZINE DERIVATIVES

[75] Inventors: Satoshi Okada, Kyoto; Kozo Sawada, Tsukuba; Akio Kuroda, Tsukuba; Shinya Watanabe, Tsukuba; Hirokazu Tanaka, Takarazuka, all of Japan

[73] Assignee: Fujisawa Pharmaceutical Co., Ltd., Osaka, Japan

[21] Appl. No.: 592,309

[22] PCT Filed: Sep. 6, 1994

[86] PCT No.: PCT/JP94/01465

§ 371 Date: May 6, 1996

§ 102(e) Date: May 6, 1996

[87] PCT Pub. No.: WO95/07279

PCT Pub. Date: Mar. 16, 1995

[30] Foreign Application Priority Data

Sep. 10, 1993 [GB] United Kingdom ........... 9318790

[51] Int. Cl.$^6$ ............ C07D 221/04; C07D 471/04; C07D 209/02
[52] U.S. Cl. ............ 546/112; 546/121; 546/200; 546/201; 540/547; 544/125; 544/362; 548/312.1; 548/453; 548/467; 548/518; 549/399; 549/403; 549/404; 549/406; 549/415
[58] Field of Search ............ 546/112, 121

[56] References Cited

FOREIGN PATENT DOCUMENTS 0519353 12/1992 European Pat. Off. .

OTHER PUBLICATIONS

"Indolizine Analogues of Indometaacin," C. Casagrande et al., *Il Farmaco*, vol. 26, No. 12 (Dec., 1971), pp. 1059–1073.

"Formation of Indolizines via Pyridinium 3–Carbomethoxyallylides", Y. Tamura et al., *Chem. Pharm. Bull.*, vol. 20, No. 5, pp. 1058–1061 (1972).

"Methods for Construction of Indolizine Nucleus," T. Uchida et al., *Synthesis*, No. 4 (Apr., 1976) pp.209–236.

*Primary Examiner*—José G. Dees
*Assistant Examiner*—Jane C. Oswecki
*Attorney, Agent, or Firm*—Oblon, Spivak, McClelland, Maier & Neustadt, P.C.

[57] ABSTRACT

A new process for preparing a compound of the formula:

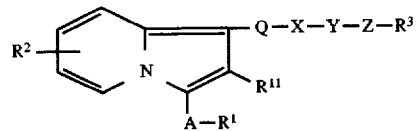

15 Claims, No Drawings

PROCESS FOR THE PREPARATION OF INDOLIZINE DERIVATIVES

This application is a 371 of PCT/US94/01465 filed Sep. 6, 1994.

The present invention relates to a new process for the preparation of indolizine derivatives which have pharmacological activities such as inhibitory activity on testosterone 5α-reductase and the like.

The process of the present invention is characterized by reacting a compound of the formula:

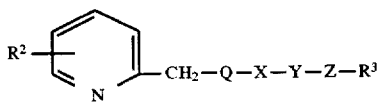

(II)

wherein $R^2$ is hydrogen, lower alkyl or halogen, $R^3$ is aryl or ar(lower)alkyl, each of which may have suitable substituent(s), substituted carbamoyl(lower) alkyl, or a group of the formula:

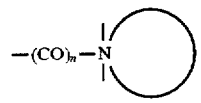

in which

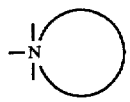

is heterocyclic group containing nitrogen atom, and n is 0 or 1,

Q is carbonyl or lower alkylene,

X is

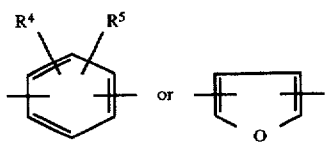

in which $R^4$ is hydrogen or lower alkyl, and $R^5$ is hydrogen, lower alkyl or Y—Z—$R^3$, Y is bond or lower alkylene, and Z is lower alkylene, lower alkenylene, —O— or

in which $R^6$ is hydrogen, lower alkyl, ar(lower)alkyl which may have suitable substituent(s) or amino protective group, or a salt thereof, with a compound of the formula:

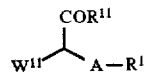

(III)

wherein $R^1$ is carboxy or protected carboxy, $R^{11}$ is hydrogen or lower alkyl, A is lower alkylene which may be substituted by oxo, or lower alkenylene, and $W^{11}$ is acid residue, or a salt thereof, to give a compound of the formula:

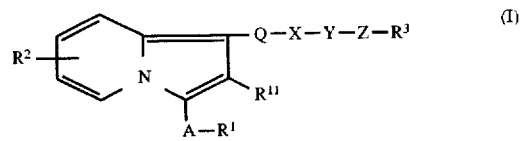

(I)

wherein $R^1$, $R^2$, $R^3$, $R^{11}$, A, Q, X, Y and Z are each as defined above, or a salt thereof.

The process of the present invention is very useful for industrially preparing the indolizine derivatives.

Suitable salts of the compounds (I), (II) and (III) are conventional non-toxic, pharmaceutically acceptable salt and may include a salt with a base or an acid addition salt such as a salt with an inorganic base, for example, an alkali metal salt (e.g. sodium salt, potassium salt, cesium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like, and the preferable example thereof is an acid addition salt.

In the above and subsequent descriptions of the present specification, suitable examples and illustrations of the various definitions which the present invention include within the scope thereof are explained in detail as follows.

The term "lower" is intended to mean 1 to 6 carbon atoms, preferably 1 to 4 carbon atoms, unless otherwise indicated.

Suitable "lower alkyl" may include straight or branched one, having 1 to 10 carbon atom(s), such as methyl, ethyl, propyl, isopropyl, butyl, isobutyl, t-butyl, pentyl, hexyl, heptyl, octyl, nonyl, decyl, and the like, preferably one having 1 to 6 carbon atoms, and more preferably one having 1 to 4 carbon atoms.

The term "halogen" means fluoro, chloro, bromo and iodo.

Suitable "lower alkylene" means straight or branched bivalent lower alkane such as methylene, ethylene, trimethylene, tetramethylene, pentamethylene, hexamethylene, propylene, and the like, which may be substituted by oxo.

Suitable "acid residue" may include halogen (e.g. fluoro, chloro, bromo, iodo), acyloxy (e.g. acetoxy, tosyloxy, mesyloxy, etc.) and the like.

Suitable "lower alkenylene" may include one having 2 to 6 carbon atoms such as vinylene, propenylene, and the like.

Suitable "aryl which may have suitable substituent(s)" may include a conventional group such as aryl (e.g. phenyl, naphthyl, etc.), substituted aryl, for example, lower alkylaryl (e.g. tolyl, xylyl, mesityl, cumenyl, isobutylphenyl, etc.), haloaryl (e.g. chlorophenyl, etc.), and the like.

"Ar(lower)alkyl" in the "ar(lower)alkyl which may have suitable substituent(s)" means straight or branched $C_1$–$C_{10}$ alkyl substituted by aryl group(s), and suitable "ar(lower) alkyl which may have suitable substituent(s)" may include a conventional group such as ar(lower)alkyl (e.g. trityl, benzhydryl, benzyl, phenethyl, naphthylmethyl, 1-phenylethyl, phenylpropyl, phenylbutyl, phenylpentyl, phenylhexyl, phenylheptyl, phenyLoctyl, phenyldecyl, 2,2-dimethyl-1-phenylpropyl, etc.), substituted [ar(lower)alkyl], for example, ar(lower)alkyl substituted by one or more substituents such as lower alkyl as mentioned above, halogen as mentioned above, cyano, carboxy, protected carboxy as mentioned below, aryl which may have suitable substituent(s) as mentioned above, amidated carboxy as mentioned below, lower alkoxy (e.g. methoxy, ethoxy, propoxy, etc.), hydroxy(lower)alkyl (e.g. hydroxyisobutyl, etc.), protected hydroxy(lower)alkyl as lower alkanoyloxy(lower)alkyl (e.g. acetoxyisobutyl, etc.), cyclo(lower)alkyl (lower)alkyl (e.g. cyclopropylmethyl), cyclobutylmethyl, etc.), lower alkenyl (e.g. vinyl, propenyl, butenyl, etc.), and lower alkynyl (e.g. ethynyl, propynyl, butynyl, etc.). Specific examples of thus defined "ar(lower)alkyl which may have suitable substituents" may be methylbenzyl, isobutylbenzyl, (methylphenyl)ethyl, (isobutylphenyl)ethyl, (methylphenyl)propyl, (isobutylphenyl)propyl, (isobutylphenyl)butyl, (methylphenyl)pentyl, (isobutylphenyl)pentyl, (isobutylphenyl)hexyl, (isobutylphenyl)heptyl, (isobutylphenyl)octyl, bis(methylphenyl)methyl, bis(propylphenyl)methyl, bis(butylphenyl)methyl, bis(isobutylphenyl)methyl, bis(chlorophenyl)methyl, (cyano) (isobutylphenyl)methyl, (carboxy) (isobutylphenyl)methyl, (benzyloxycarbonyl) (isobutylphenyl)methyl, (N,N-diethylcarbamoyl) (isobutylphenyl)methyl, (t-butylcarbamoyl) (isobutylphenyl)methyl, (phenylcarbamoyl) (isobutylphenyl)methyl, (isobutylphenylcarbamoyl) (isobutylphenyl)methyl, (butylcarbamoyl) (isobutylphenyl) methyl, (heptylcarbamoyl) (isobutylphenyl)methyl, (ethoxy) (isobutylphenyl)ethyl, (isobutylphenyl) trifluorobutyl, (phenyl) (isobutylphenyl)methyl, [(isobutyl) (methoxy)phenyl]pentyl, [(fluoro) (isobutyl)phenyl]pentyl, [(fluoro) (hydroxyisobutyl)phenyl]pentyl, [(fluoro) (acetoxyisobutyl)phenyl]pentyl, (cyclopropylmethylphenyl) butenyl, (isobutylphenyl)butynyl, (isobutylphenyl)butenyl, (isobutylphenyl)pentenyl, etc.], and the like.

Suitable "amino protective group" may be a conventional protective group, which is used in the field of organic chemistry, that is, may include acyl such as lower alkanoyl (e.g. formyl, acetyl, propionyl, butyryl, isobutyryl, valeryl, isovaleryl, pivaloyl, hexanoyl, etc.), lower alkoxycarbonyl (e.g. methoxycarbonyl, ethoxycarbonyl, propoxycarbonyl, butoxycarbonyl, t-butoxycarbonyl, etc.), and the like.

Suitable "protected carboxy" may include an esterified carboxy group.

Suitable examples of the ester moiety of an "esterified carboxy" may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy (lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.), lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene (lower)alkyl ester, or (5-lower alkyl-2-oxo-1,3-dioxol-4-yl) (lower)alkyl ester (e.g. (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

Preferable examples of the esterified carboxy as mentioned above may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.).

Suitable "heterocyclic group containing nitrogen atom" may include saturated or unsaturated monocyclic or polycyclic heterocyclic group containing at least one nitrogen atom. Especially preferable heterocyclic group may be 5- or 6-membered aliphatic heteromonocyclic group (e.g. morpholinyl, pyrrolidinyl, imidazolidinyl, piperidyl, piperazinyl, etc.), unsaturated condensed heterocyclic group such as dibenzo[6- or 7-membered unsaturated] heteromonocyclic group (e.g. phenoxazinyl, phenothiazinyl, 10,11-dihydro-5H-dibenzoazepinyl, etc.), and the like.

Suitable "substituted carbamoyl(lower)alkyl" means carbamoyl(lower)alkyl, in which the carbamoyl moiety is substituted by one or two substituent(s), and suitable substituent may include a conventional group such as lower alkyl as mentioned above, aryl which may have suitable substituent(s) as mentioned above. Specific examples of thus defined "substituted carbamoyl(lower)alkyl" may be butylcarbamoylmethyl, 1-(heptylcarbamoyl)ethyl, isobutylphenylcarbamoylmethyl, 1-(isobutylphenylcarbamoyl)ethyl, and the like.

Particularly, the preferred embodiments of $R^1$, $R^2$, $R^3$, $R^{11}$, A, Q, X, Y and Z are as follows.

$R^1$ is carboxy;

esterified carboxy such as lower alkoxycarbonyl, more preferably $C_1$–$C_4$ alkoxycarbonyl (e.g. methoxycarbonyl, ethoxycarbonyl, etc.); or ar(lower) alkoxycarbonyl, more preferably mono- or di- or triphenyl($C_1$–$C_4$)-alkoxycarbonyl (e.g. benzyloxycarbonyl, etc.)

$R^2$ is hydrogen;

lower alkyl, more preferably $C_1$–$C_4$ alkyl (e.g. methyl, etc.); or halogen (e.g. chloro, etc.), $R^3$ is aryl which may be substituted by lower alkyl, more preferably phenyl substituted by $C_1$–$C_4$ alkyl (e.g. isobutylphenyl, etc.); ar(lower)alkyl which may be substituted by one or more substituents selected from the group consisting of lower alkyl, halogen, cyano, carboxy, protected carboxy, amidated carboxy, lower alkoxy, hydroxy(lower)alkyl, protected hydroxy (lower)alkyl, cyclo(lower)alkyl, lower alkenyl, and lower alkynyl, more preferably mono- or di- or triphenyl(lower)alkyl which may be substituted by one to four groups selected from lower alkyl, halogen, cyano, carboxy, phenyl(lower)alkoxycarbonyl, mono or di(lower)alkylcarbamoyl, phenylcarbamoyl, lower alkylphenylcarbamoyl, lower alkoxy, hydroxy(lower)alkyl, lower alkanoyloxy(lower)alkyl, cyclo(lower)alkyl(lower)alkyl, lower alkenyl, and lower alkynyl, most preferably mono- or di- or triphenyl($C_1$–$C_{10}$)alkyl which may be substituted by one to four groups selected from ($C_1$–$C_{10}$)alkyl, halogen, cyano, carboxy, phenyl($C_1$–$C_4$)alkoxycarbonyl, mono or di($C_1$–$C_{10}$) alkylcarbamoyl, phenylcarbamoyl, ($C_1$–$C_4$) alkylphenylcarbamoyl, ($C_1$–$C_4$)alkoxy, hydroxy ($C_1$–$C_4$)alkyl, ($C_1$–$C_4$)alkanoyloxy($C_1$–$C_4$)alkyl, cyclo ($C_3$–$C_6$)alkyl($C_1$–$C_4$)alkyl, ($C_2$–$C_4$)alkenyl and ($C_2$–$C_4$)alkynyl, (e.g. benzyl, isobutylbenzyl, (isobutylphenyl)ethyl, (isobutylphenyl)propyl, (isobutylphenyl)butyl, (isobutylphenyl)pentyl, (isobutylphenyl)hexyl, (isobutylphenyl)heptyl, (isobutylphenyl)octyl, bis(isobutylphenyl)methyl, bis (chlorophenyl)methyl, (cyano) (isobutylphenyl) methyl, (carboxy) (isobutylphenyl)methyl, (benzyloxycarbonyl) (isobutylphenyl)methyl, (N,N-diethylcarbamoyl) (isobutylphenyl)methyl, (t-butylcarbamoyl) (isobutylphenyl)methyl, (phenylcarbamoyl) (isobutylphenyl)methyl, (isobutylphenylcarbamoyl) (isobutylphenyl)methyl, (butylcarbamoyl) (isobutylphenyl)methyl, (heptylcarbamoyl) (isobutylphenyl)methyl, (ethoxy) (isobutylphenyl)ethyl, (isobutylphenyl) (trifluoro) butyl, (phenyl) (isobutylphenyl)methyl, [(isobutyl) (methoxy)phenyl]pentyl, [(fluoro) (isobutyl)phenyl] pentyl, [(fluoro) (hydroxyisobutyl)phenyl]pentyl, [(fluoro) (acetoxyisobutyl)phenyl]pentyl, (cyclopropylmethylphenyl)butenyl, (isobutylphenyl) butynyl, (isobutylphenyl)butenyl, (isobutylphenyl) pentenyl, etc.); carbamoyl(lower)alkyl, in which he carbamoyl moiety is substituted by one or two substituent(s) selected from the group consisting of lower alkyl and lower alkylphenyl, more preferably ($C_1$–$C_{10}$)alkylcarbamoyl-($C_1$–$C_4$)alkyl or ($C_1$–$C_4$) alkylphenylcarbamoyl($C_1$–$C_4$)-alkyl (e.g. heptylcarbamoylethyl, isobutylphenylcarbamoylmethyl, isobutylphenylcarbamoylethyl, etc.); 5- or 6-membered aliphatic heteromonocycliccarbonyl (e.g. piperidylcarbonyl, etc.); or unsaturated condensed heterocyclic group (e.g. phenoxazinyl, phenothiazinyl, 10,11-dihydro-5H-dibenzo[b,f]azepinyl, etc.), $R^{11}$ is hydrogen; or lower alkyl, more preferably $C_1$–$C_4$ alkyl (e.g. methyl, etc.), A is lower alkylene which may be substituted by oxo, more preferably $C_1$–$C_4$ alkylene which may be substituted by oxo (e.g. ethylene, trimethylene, oxotrimethylene, etc.); or lower alkenylene, more preferably $C_2$–$C_4$ alkenylene (e.g. propenylene, etc.), Q is carbonyl; or lower alkylene, more preferably $C_1$–$C_4$ alkylene (e.g. methylene, etc.), X is

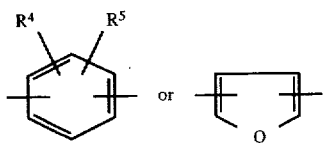

in which
$R^4$ is hydrogen; or lower alkyl, more preferably $C_1$–$C_4$ alkyl (e.g. methyl, etc.), $R^5$ is hydrogen; lower alkyl, more preferably $C_1$–$C_4$ alkyl (e.g. methyl, etc.); or ar(lower)alkylamino which may be substituted by the group(s) selected from lower alkyl or lower alkoxycarbonyl, more preferably $C_1$–$C_4$ alkylbenzylamino or N-$C_1$–$C_4$ alkoxycarbonyl-N-$C_1$–$C_4$ alkylbenzylamino (e.g. isobutylbenzylamino, N-t-butoxy-carbonyl-N-isobutylbenzylamino, etc.), Y is bond; or lower alkylene, more preferably $C_1$–$C_4$ alkylene (e.g. methylene, etc.), and Z is lower alkylene, more preferably $C_1$–$C_4$ alkylene (e.g. methylene, etc.); lower alkenylene, more preferably $C_2$–$C_4$ alkenylene (e.g. vinylene, etc.);

—O—; or

in which $R^6$ is hydrogen; lower alkyl, preferably $C_1$–$C_4$ alkyl (e.g. methyl, ethyl, etc.); lower alkoxycarbonyl, preferably $C_1$–$C_4$ alkoxycarbonyl (e.g. t-butoxycarbonyl, etc.); ar(lower)alkyl which may be substituted by lower alkyl, more preferably mono- or di- or triphenyl(lower)alkyl which may be substituted by lower alkyl, most preferably mono- or di- or triphenyl($C_1$–$C_6$)alkyl which may be substituted by $C_1$–$C_4$ alkyl (e.g. benzyl, isobutylbenzyl, etc.).

The process for preparing the object compound (I) of the present invention is explained in detail in the following.

PROCESS

The object compound (I) or a salt thereof can be prepared by reacting the compound (II) or a salt thereof with the compound (III) or a salt thereof.

This reaction is usually carried out in a solvent such as alcohol [e.g. methanol, ethanol, etc.], dichloromethane, benzene, N,N-dimethylformamide, tetrahydrofuran, diethyl ether or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], alkali metal hydride (e.g. sodium hydride, potassium hydride, etc.), tri(lower)alkylamine [e.g. trimethylamine, triethylamine, diisopropylethylamine, etc.], pyridine or its derivative [e.g. picolin, lutidine, 4-dimethylaminopyridine, etc.], or the like. In case that the base to be used is liquid, it can also be used as a solvent.

The reaction temperature is not critical, and the reaction can be carried out under cooling, at room temperature or under warming or heating.

The object compound (I) of the present invention can be isolated and purified in a conventional manner, for example, extraction, precipitation, fractional crystallization, recrystallization, chromatography, and the like.

The object compound (I) thus obtained can be converted to its salt by a conventional method.

The object compound (I) of the present invention is useful as a testosterone 5α-reductase inhibitor and effective to testosterone 5α-reductase mediated diseases such as prostatism, prostatic hypertrophy, prostatic cancer, alopecia, hirsutism (e.g. female hirsutism, etc.), androgenic alopecia (or male-pattern baldness), acne (e.g. acne vulgaris, pimple etc.), other hyperandrogenism, and the like.

For therapeutic or preventive administration, the object compound (I) of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparation may be in solid form such as tablet, granule, powder, capsule, or liquid form such as solution, suspension, syrup, emulsion, lemonade, lotion and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases or conditions, a kind of the compound (I) to be applied, etc. In general amounts between 0.01 mg and about 500 mg or even more per day may be administered to a patient. An average single dose of about 0.05 mg, 0.1 mg, 0.25 mg, 0.5 mg, 1 mg, 20 mg, 50 mg, 100 mg of the object compound (I) of the present invention may be used in treating diseases.

The following Preparations and Examples are given for the purpose of illustrating the present invention.

PREPARATION 1

To a solution of adipic acid monomethyl ester (8.0 g) in carbon tetrachloride (5 ml) was added thionyl chloride (14.4 ml). The mixture was stirred at 65° C. for 30 minutes. N-Bromosuccinimide (10.7 g), carbon tetrachloride (25 ml) and 48; hydrobromic acid aqueous solution (0.5 ml) was added to the mixture. The mixture was refluxed for 1.5 hours, cooled at room temperature and filtered off. The filtrate was evaporated and distillated at reduced pressure to give methyl 5-bromo-5-chloroformylpentanoate as an oil (9.02 g).

bp : 87°–91° C./0.5 mmHg

NMR (CDCl$_3$, δ) : 4.55 (1H, m), 3.70 (3H, s), 2.40 (2H, t, J=7Hz), 2.0–2.3 (2H, m), 1.6–2.0 (2H, m)

PREPARATION 2

To a solution of methyl 5-bromo-5-chloroformylpentanoate (2.57 g) in diethyl ether (15 ml) was added a mixture of phenol (0.94 g) and diisopropylethylamine (1.30 g) in diethyl ether (10 ml). The mixture was stirred at room temperature for 15 minutes and poured into ice water and diluted hydrochloric acid. The organic layer was washed with water, dried over magnesium sulfate and evaporated. The residue was chromatographed on silica gel eluting with a mixture of n-hexane and ethyl acetate (5:1) to give methyl 5-bromo-5-phenoxycarbonylpentanoate as an oil (2.33 g).

NMR (CDCl$_3$, δ) : 7.3–7.5 (2H, m), 7.2–7.3 (1H, m), 7.1–7.2 (2H, m), 4.43 (1H, m), 3.70 (3H, s), 2.40 (2H, t, J=7Hz), 2.1–2.4 (2H, m), 1.7–2.0 (2H, m)

PREPARATION 3

To a solution of methyl 5-bromo-5-phenoxycarbonylpentanoate (1.0 g) in tetrahydrofuran (20 ml) was added a 1.0M solution of lithium tri-tert-butoxyaluminohydride in tetrahydrofuran (3.1 ml) at 0° C. The mixture was stirred for 2 hours and poured into a mixture of diluted hydrochloric acid and ethyl acetate. The organic layer was washed with brine, dried over magnesium sulfate and evaporated. The residue was chromatographed on silica gel eluting with a mixture of n-hexane and ethyl acetate (5:1) to give methyl 5-bromo-5-formylpentanoate as an oil (0.64 g).

NMR (CDCl$_3$, δ) : 9.47 (1H, d, J=3Hz), 4.25 (1H, m), 3.68 (3H, s), 2.40 (2H, t, J=7Hz), 1.7–2.2 (4H, m)

PREPARATION 4

To a solution of 1-(R)-(4-isobutylphenyl)butanol (1.13 g), methyl 4-hydroxybenzoate (917 mg) and triphenylphosphine (1.58 g) in toluene (40 ml) and tetrahydrofuran (10 ml) was added diethyl azodicarboxylate (0.95 ml) at −20° C. The mixture was stirred at −15°—−20° C. for 1.5 hours and then added water (0.5 ml). The mixture was evaporated, dissolved in a mixture of n-hexane and ethyl acetate (4:1), filtered off and evaporated. The residue was chromatographed on silica gel eluting with a mixture of n-hexane and dichloromethane (1:1) to give methyl 4-[1-(S)-(4-isobutylphenyl)butoxy]benzoate as an oil (1.48 g).

NMR (CDCl$_3$, δ) : 7.89 (1H, d, J=9Hz), 7.22 (2H, d, J=9Hz), 7.10 (2H, d, J=9Hz), 6.85 (2H, d, J=9Hz), 5.15 (1H, m), 3.83 (3H, s), 2.42 (2H, d, J=7Hz), 1.9–2.0 (1H, m), 1.7–1.9 (2H, m), 1.3–1.6 (2H, m), 0.95 (3H, t, J=7Hz), 0.89 (6H, d, J=7Hz)

PREPARATION 5

To a solution of methyl 4-[1-(S)-(4-isobutylphenyl)-butoxy]benzoate (283 mg) and 2-methylpyridine (0.09 ml) in tetrahydrofuran (5 ml) was added 1.0M solution of lithium bis(trimethylsilyl)amide in tetrahydrofuran (2.7 ml) at 0° C. The mixture was stirred for 18 hours at room temperature. Acetic acid (0.18 ml) and ethyl acetate (15 ml) was added to the mixture. The mixture was washed with water and aqueous solution of sodium bicarbonate, dried over magnesium sulfate and evaporated. The residue was chromatographed on silica gel eluting with a mixture of n-hexane and ethyl acetate (2:1) to give 4-[1-(S)-(4-isobutylphenyl)butoxy]phenyl 2-pyridylmethyl ketone as a yellow oil (216 mg).

NMR (CDCl$_3$, δ) : 8.52 (1H, d, J=5Hz), 7.94 (2H, d, J=9Hz), 7.5–7.7 (1H, m), 7.0–7.3 (6H, m), 6.88 (2H, d, J=9Hz), 5.15 (1H, m), 4.39 (2H, s), 2.44 (2H, d, J=7Hz), 1.9–2.1 (1H, m), 1.7–1.9 (2H, m), 1.3–1.6 (2H, m), 0.94 (3H, t, J=7Hz), 0.89 (6H, d, J=7Hz)

EXAMPLE 1

To a solution of 4-[1-(S)-(4-isobutylphenyl)butoxy]-phenyl 2-pyridylmethyl ketone (211 mg) and methyl 5-bromo-5-formylpentanoate (123 mg) in 1,4-dioxane (3 ml) was added diisopropylethyl amine (0.1 ml). The mixture was stirred at 80° C. for 3.5 hours and poured into a mixture of ethyl acetate and diluted hydrochloric acid. The organic layer was separated, washed with water, dried over magnesium sulfate and evaporated. The residue was chromatographed on silica gel eluting with the mixture of n-hexane and ethyl acetate (2:1) to give methyl 4-[1-[4-[1-(S)-(4-isobutylphenyl)butoxy]benzoyl]lindolizin-3-yl]butyrate as an oil (187 mg).

NMR (CDCl₃, δ) : 8.43 (1H, d, J=9Hz), 7.98 (1H, d, J=7Hz), 7.73 (2H, d, J=9Hz), 7.25 (2H, d, J=9Hz), 7.11 (2H, d, J=9Hz), 7.1–7.2 (1H, m), 6.8–7.0 (4H, m), 5.18 (1H, m), 3.68 (3H, s), 2.89 (2H, t, J=7Hz), 2.4–2.5 (4H, m), 1.9–2.15 (3H, m), 1.7–1.9 (2H, m), 1.4–1.6 (2H, m), 0.98 (3H, t, J=7Hz), 0.90 (6H, d, J=7Hz)

EXAMPLE 2

To a solution of methyl 4-[1-[4-[1-(S)-(4-isobutylphenyl)butoxy]benzoyl]indolizin-3-yl]butyrate (182 mg) in ethanol (4 ml) was added 1N aqueous solution of sodium hydroxide (0.6 ml). The mixture was stirred at 50° C. for 40 minutes, and then poured into a mixture of ethyl acetate and diluted hydrochloric acid. The organic layer was separated, washed with water, dried over magnesium sulfate and evaporated. The residue was crystallized with diisopropyl ether to give 4-[1-[4-[1-(S)-(4-isobutylphenyl)butoxy]benzoyl]indolizin-3-yl]butyric acid as white powder (89 mg).

NMR (CDCl₃, δ) : 8.42 (1H, d, J=9Hz), 7.96 (1H, d, J=7Hz), 7.72 (2H, d, J=9Hz), 7.05–7.3 (5H, m), 6.8–6.95 (4H, m), 5.16 (1H, m), 2.88 (2H, t, J=7.5Hz), 2.4–2.55 (4H, m), 1.7–2.15 (5H, m), 1.3–1.65 (2H, m), 0.8–1.05 (9H, m)

We claim:

1. A process for preparing a compound of the formula:

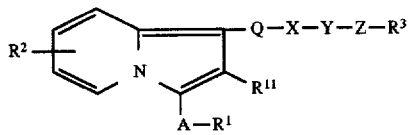

wherein $R^1$ is carboxy or protected carboxy, $R^2$ is hydrogen, lower alkyl or halogen, $R^3$ is aryl or ar(lower)alkyl, each of which may be optionally substituted; or carbamoyl(lower)alkyl, in which the carbamoyl moiety is substituted by 1 or 2 substituent(s) selected from the group consisting of lower alkyl and lower alkyl phenyl; or a group of the formula:

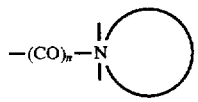

in which

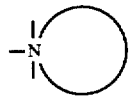

is a heterocyclic group containing nitrogen, and n is 0 or 1, $R^{11}$ is hydrogen or lower alkyl, A is lower alkylene which may be substituted by oxo or lower alkylene, Q is carbonyl or lower alkylene, X is

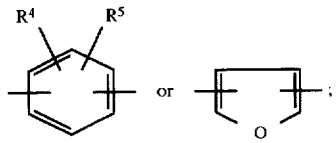

in which $R^4$ is hydrogen or lower alkyl, and $R^5$ is hydrogen, lower alkyl or Y—Z—R³.

Y is a direct bond or lower alkylene, and

Z is lower alkylene, lower alkenylene,

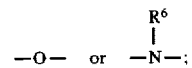

in which $R^6$ is hydrogen, lower alkyl, or ar(lower)alkyl which may be optionally substituted or an amino protective group, or a salt thereof, which process comprises:

reacting a compound of the formula:

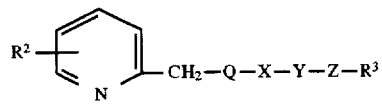

wherein $R^2$, $R^3$, Q, X, Y and Z are each as defined above, or a salt thereof, with a compound of the formula:

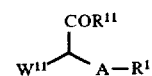

wherein $R^1$, $R^{11}$ and A are each as defined above, and $W^{11}$ is halogen or acyloxy, or a salt thereof.

2. The process of claim 1, wherein $R^3$ is aryl or substituted aryl consisting of phenyl, naphthyl, tolyl, xylyl, mesityl, cumenyl, isobutylphenyl and chlorophenyl.

3. The process of claim 1, wherein $R^3$ is ar(lower)alkyl and is selected from the group consisting of trityl, benzhydryl, benzyl, phenethyl, naphthylmethyl, 1-phenylethyl, phenylpropyl, phenylbutyl, phenylpentyl, phenylhexyl, phenyheptyl, phenyloctyl, phenyldecyl and 2,2-dimethyl-1-phenylpropyl.

4. The process of claim 1, wherein $R^3$ is ar(lower)alkyl which is substituted by lower alkyl, halogen, cyano, carboxy, protected carboxy, aryl, amidated carboxy, lower alkoxy, hydroxy(lower)alkyl, protected hydroxy(lower)alkyl and cyclo(lower)alkyl(lower)alkyl.

5. The process of claim 1, which is effected in the presence of an inert solvent.

6. The process of claim 1, which is effected in the presence of an organic or inorganic base.

7. The process of claim 1, wherein said heterocyclic group containing nitrogen is selected from the group consisting of 5- and 6-membered aliphatic heteromonocyclic groups and 6- and 7-membered unsaturated heteromonocyclic groups.

8. The process of claim 7, wherein said 5- and 6-membered aliphatic heteromonocyclic groups are selected from the group consisting of morpholinyl, pyrrolidinyl, imidazolidinyl, piperidyl and piperazinyl.

9. The process of claim 7, wherein said 6- and 7-membered unsaturated heteromonocylic groups are selected from the group consisting of phenoxazinyl, phenothiazinyl, and 10,11-dihydro-5H-dibenzoazepinyl.

10. The process of claim 1, which comprises reacting 4-phenyl 2-pyridylmethyl ketone with methyl 5-bromo-5-formyl pentanoate to produce methyl 4-benzoyl butyrate.

11. A compound of the formula:

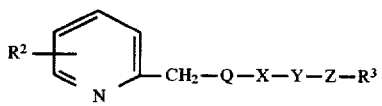

wherein $R^2$ is hydrogen, lower alkyl or halogen, $R^3$ is aryl or ar(lower)alkyl, each of which may be optionally substituted; or carbamoyl(lower)alkyl, in which the carbamoyl moiety is substituted by 1 or 2 substituent(s) selected from the group consisting of lower alkyl or lower alkyl phenyl; or a group of the formula:

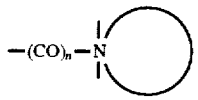

in which

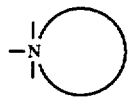

is a heterocyclic group containing nitrogen, and n is 0 or 1,

Q is carbonyl or lower alkylene, X is

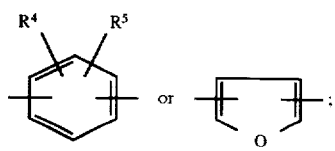

in which $R^4$ is hydrogen or lower alkyl, and $R^5$ is hydrogen, lower alkyl or Y—Z—$R^3$,
Y is a direct bond or lower alkylene, and
Z is lower alkylene, lower alkenylene,

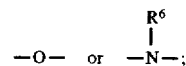

in which $R^6$ is hydrogen, lower alkyl, or ar(lower)alkyl which may be optionally substituted, or an amino protective group, or a salt thereof.

12. The compound of claim 11, wherein said heterocyclic group containing nitrogen is selected from the group consisting of 5- and 6-membered aliphatic heteromonocyclic groups and 6- and 7-membered unsaturated heteromonocyclic groups.

13. The compound of claim 11, wherein said 5- and 6-membered aliphatic heteromonocyclic groups are selected from the group consisting of morpholinyl, pyrrolidinyl, imidazolidinyl, piperidyl and piperazinyl.

14. The compound of claim 11, wherein said 6- and 7-membered unsaturated heteromonocylic groups are selected from the group consisting of phenoxazinyl, phenothiazinyl, and 10,11-dihydro-5H-dibenzoazepinyl.

15. The compound of claim 11, wherein said salt comprises an alkali metal salt, an alkaline earth metal salt, an ammonium salt, an organic amine salt, an inorganic acid addition salt, an organic carboxylic or sulfonic acid addition salt, or a salt of a basic or acidic amino acid.

* * * * *